US010074927B1

(12) United States Patent
Ono

(10) Patent No.: US 10,074,927 B1
(45) Date of Patent: Sep. 11, 2018

(54) ELECTRICAL CONNECTOR AND METHOD FOR MANUFACTURING ELECTRICAL CONNECTOR

(71) Applicant: SMK Corporation, Tokyo (JP)

(72) Inventor: Naoyuki Ono, Chiba (JP)

(73) Assignee: SMK Corporation, Tokyo (JP)

(*) Notice: Subject to any disclaimer, the term of this patent is extended or adjusted under 35 U.S.C. 154(b) by 0 days.

(21) Appl. No.: 15/681,438

(22) Filed: Aug. 21, 2017

(30) Foreign Application Priority Data

Mar. 13, 2017 (JP) .................................. 2017-46887

(51) Int. Cl.
| | |
|---|---|
| *H01R 13/648* | (2006.01) |
| *H01R 13/52* | (2006.01) |
| *H01R 13/6581* | (2011.01) |
| *H01R 43/24* | (2006.01) |
| *H01R 13/405* | (2006.01) |
| *H01R 13/504* | (2006.01) |
| *H01R 107/00* | (2006.01) |
| *B05D 1/36* | (2006.01) |
| *C07F 7/18* | (2006.01) |

(52) U.S. Cl.
CPC ....... *H01R 13/5202* (2013.01); *H01R 13/405* (2013.01); *H01R 13/504* (2013.01); *H01R 13/521* (2013.01); *H01R 13/6581* (2013.01); *H01R 43/24* (2013.01); *B05D 1/36* (2013.01); *C07F 7/18* (2013.01); *H01R 2107/00* (2013.01)

(58) Field of Classification Search
CPC ........................ H01R 13/5216; H01R 13/6594
USPC ................... 439/736, 933, 607, 4, 607.55
See application file for complete search history.

(56) References Cited

U.S. PATENT DOCUMENTS

| | | | | | |
|---|---|---|---|---|---|
| 3,922,477 | A | * | 11/1975 | Glowacz .............. | H01R 13/521 174/18 |
| 6,210,226 | B1 | * | 4/2001 | Zhu ........................ | H01R 24/64 439/607.4 |
| 6,554,648 | B2 | * | 4/2003 | Shi ..................... | H01R 13/6582 439/607.55 |
| 7,568,932 | B2 | * | 8/2009 | O'Connor .............. | H01R 4/029 439/271 |
| 7,931,497 | B2 | * | 4/2011 | Yang .................. | H01R 13/6594 439/362 |
| 8,512,074 | B2 | * | 8/2013 | Frey ..................... | H01R 13/523 439/279 |

(Continued)

FOREIGN PATENT DOCUMENTS

JP         2015-111524 A         6/2015

OTHER PUBLICATIONS

Office Action issued for counterpart Japanese Application 2017-046887, issued by the Japan Patent Office dated Jun. 21, 2017.

*Primary Examiner* — Neil Abrams

(57) ABSTRACT

An electrical connector and a method for manufacturing the electrical connector are provided to make the electrical connector watertight, simplify assembly, and suppress an increase in manufacturing cost. The electrical connector includes an insulating housing, and conductive contacts held by the housing. The conductive contacts including connection portions that are exposed on a front side of the housing and connect to mating contacts of a mating connector, and terminal portions that protrude behind the housing. A portion of the housing in close contact with the contacts along the outer peripheries of the contacts contains a silane coupling agent.

6 Claims, 10 Drawing Sheets

(56) References Cited

U.S. PATENT DOCUMENTS

| | | | | |
|---|---|---|---|---|
| 9,716,349 B1* | 7/2017 | Wang | ................ | H01R 13/6594 |
| 9,742,121 B2* | 8/2017 | Hayashi | ............. | H01R 13/6585 |
| 9,768,535 B1* | 9/2017 | Wu | ...................... | H01R 12/707 |
| 9,917,405 B2* | 3/2018 | Ju | ...................... | H01R 13/6585 |
| 2017/0338585 A1* | 11/2017 | Wang | ................ | H01R 13/5202 |
| 2017/0373442 A1* | 12/2017 | Qiu | .................... | H01R 13/6581 |
| 2018/0048088 A1* | 2/2018 | Ono | ................. | H01R 13/5202 |
| 2018/0175559 A1* | 6/2018 | Zhao | ................. | H01R 13/6591 |

* cited by examiner

ELECTRICAL CONNECTOR AND METHOD FOR MANUFACTURING ELECTRICAL CONNECTOR

CROSS REFERENCE TO RELATED APPLICATION

The contents of the following Japanese patent application are incorporated herein by reference, Japanese Patent Application No. 2017-46887 filed on Mar. 13, 2017.

FIELD

The present invention relates to an electrical connector having a watertight function and a method for manufacturing the electrical connector.

BACKGROUND

Conventionally, electrical connectors attached to electronic devices have been required to have a watertight function of making the interior of the electronic devices watertight from outside. To fit to a mating connector, such an electrical connector includes a fitting portion exposed to outside the casing of the electronic device. Gaps between conductive contacts arranged on the fitting portion and an insulating housing holding the contacts need to be made watertight.

If an electrical connector is formed by integrally molding a housing and contacts, the housing and the contacts are not in close contact with each other. There are gaps between the housing and the contacts, and a desired watertight effect is not available. If contacts having fine grooves in the surface and a housing are integrally molded to form an electrical connector, a desired watertight effect can be obtained. However, the need to machine the contacts increases product and manufacturing costs.

Under the circumstances, Patent Literature 1 discloses a configuration of an electrical connector having a watertight function, in which a rear end portion of a housing is provided with a sealing material formed by filling and curing a resin material such as a potting material. The electrical connector according to Patent Literature 1 can be made watertight by sealing gaps between the housing and terminals arranged on the housing with the sealing material provided in the rear end portion of the housing.

CITATION LIST

Patent Literature

Patent Literature 1: Japanese Patent Application Laid-Open No. 2015-111524

SUMMARY

Technical Problem

According to Patent Literature 1, the electrical connector needs to be held so that the sealing material will not drip on unwanted portions during filling of the sealing material. There is also a need to wait for the sealing material to cure. The electrical connector thus has a problem that its complex assembly steps complicate the assembly and cause an increase in manufacturing cost.

Solution to Problem

An object of the present invention is to provide an electrical connector which can be made watertight, of which assembly can be simplified, and of which an increase in manufacturing cost can be suppressed, and a method for manufacturing the electrical connector.

An electrical connector according to one aspect of the present invention includes: an insulating housing; and a conductive contact held by the housing, the contact including a connection portion that is exposed on a front side of the housing and connects to a mating contact of a mating connector, and a terminal portion that protrudes behind the housing, a portion of the housing in close contact with the contact along an outer periphery of the contact containing a silane coupling agent.

A method for manufacturing an electrical connector according to another aspect of the present invention is a method for manufacturing an electrical connector, the electrical connector including an insulating housing and a conductive contact held by the housing, the contact including a connection portion that is exposed on a front side of the housing and connects to a mating contact of a mating connector, and a terminal portion that protrudes behind the housing, the method including: integrally molding the housing and the contact, the housing being formed of a first housing containing a silane coupling agent and a second housing containing no silane coupling agent, and simultaneously forming the first housing holding the contact at a predetermined temperature; and melting the first housing, after formed, again at a temperature higher than the predetermined temperature so that the first housing makes close contact with the contact along an outer periphery of the contact.

A liquid intruding from outside from the front into a rear portion through a gap between the contact and the housing is blocked by the silane coupling agent-containing portion of the housing in close contact with the contact along the outer periphery of the contact. The electrical connector can thus be made watertight without special machining on the contact and without using a sealing material such as a potting material.

According to the aspect(s) of the present invention, an electrical connector can be made watertight, assembly can be simplified, and an increase in manufacturing cost can be suppressed.

DESCRIPTION OF EMBODIMENTS

Figure 1:
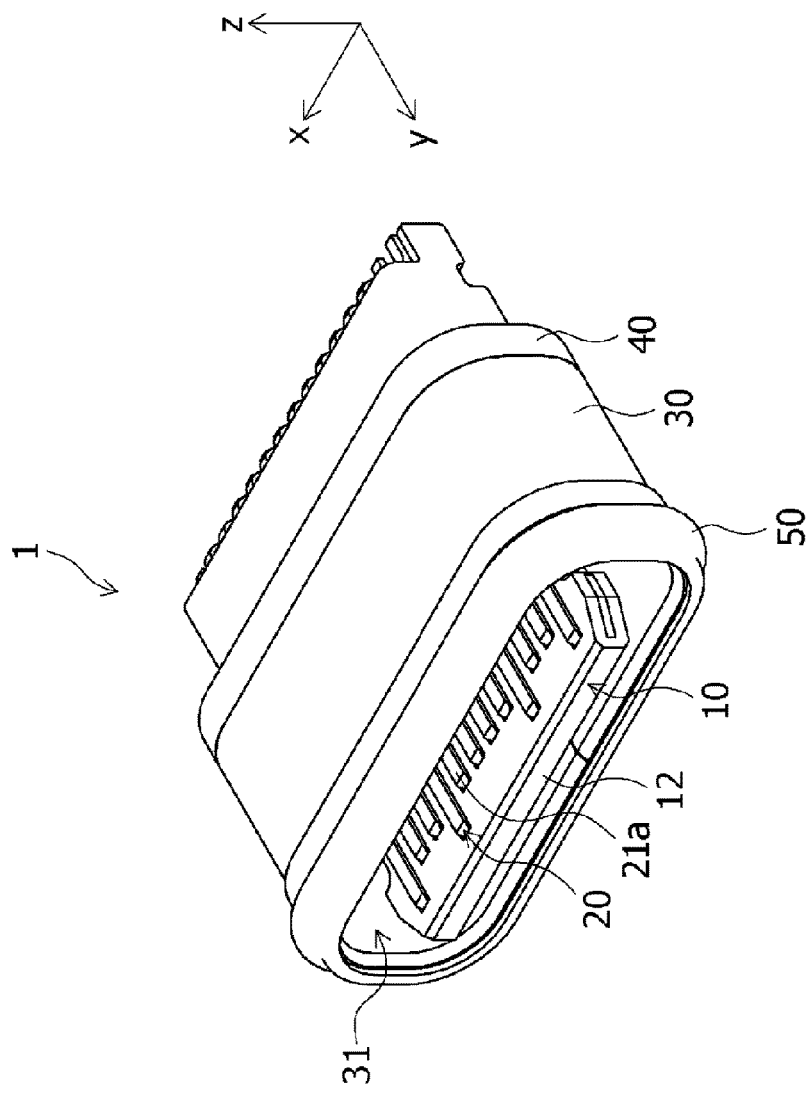
FIG. 1 is a perspective view of an electrical connector according to a first embodiment of the present invention.

Electrical connectors according to embodiments of the present invention will be described in detail below with reference to the drawings as appropriate. In the drawings, an x-axis, a y-axis, and a z-axis constitute a three-axis orthogonal coordinate system. In the following description, a positive direction of the y-axis will be referred to as a front direction, a negative direction of the y-axis as a rear direction, the direction of the x-axis as a horizontal direction, a positive direction of the z-axis as an upward direction, and a negative direction of the z-axis as a downward direction.

First Embodiment

<Configuration of Electrical Connector>

Figure 2:
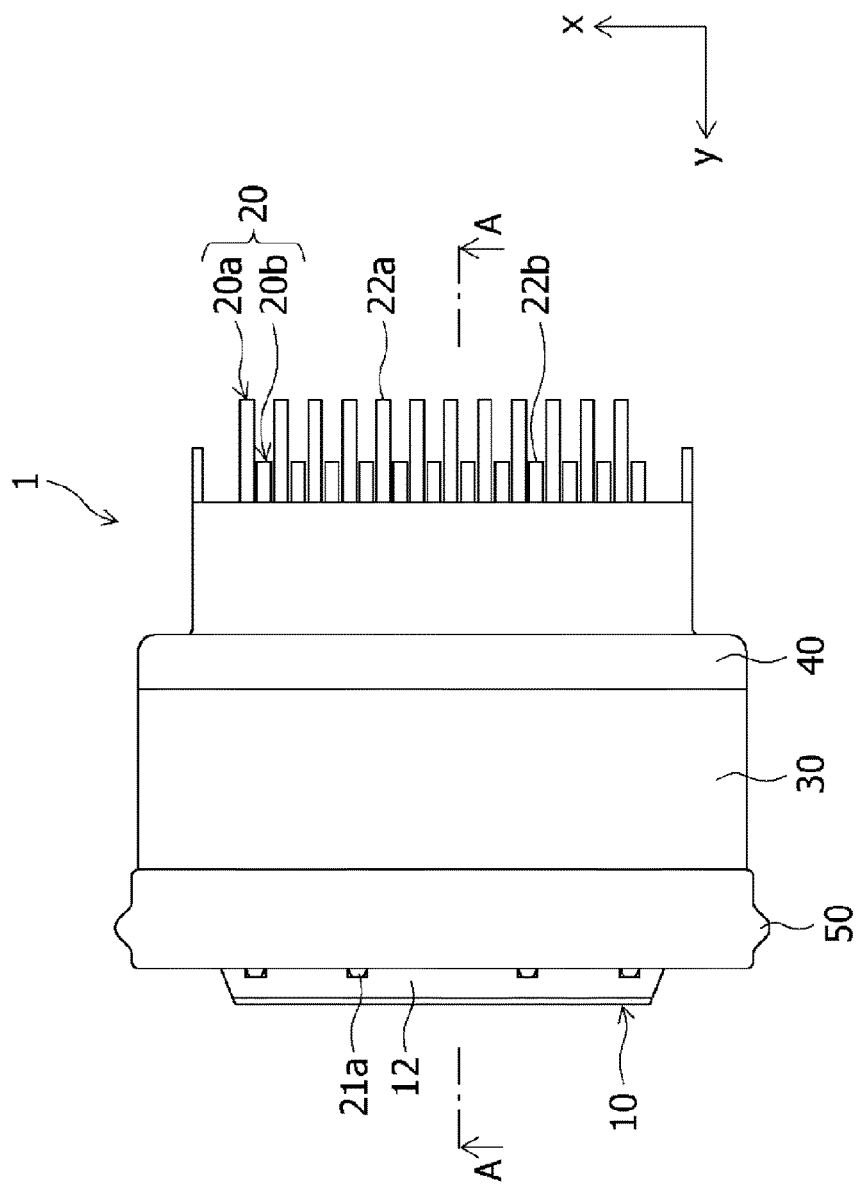
FIG. 2 is a plan view of the electrical connector according to the first embodiment of the present invention.

A configuration of an electrical connector 1 according to a first embodiment of the present invention will be described in detail below with reference to FIGS. 1 to 3.

The electrical connector 1 according to the present embodiment includes a housing 10, contacts 20, a front shell member 30, a rear shell member 40, an external watertight member 50, and a shielding plate 60.

The housing 10 is formed of an insulating material and holds the contacts 20. A portion of the housing 10 in close contact with the contacts 20 along the outer peripheries of the contacts 20 contains a silane coupling agent. The housing 10 contains no silane coupling agent in its rear end portion where the contacts 20 protrude to the rear. The silane coupling agent includes reaction groups chemically bondable to an inorganic material and reaction groups chemically bondable to an organic material, and has a property capable of bonding an organic material to an inorganic material.

The housing 10 includes a main body portion 11 and a plate-like portion 12.

The main body portion 11 includes a front protruding portion 111, a rear protruding portion 112, and an outward protruding portion 113. The front protruding portion 111 holds the contacts 20 and protrudes to the front. The rear protruding portion 112 protrudes to the rear. The outward protruding portion 113 lies between the front protruding portion 111 and the rear protruding portion 112, and protrudes outward compared to the front protruding portion 111 and the rear protruding portion 112. The outward protruding portion 113 includes a step portion 114.

The rear protruding portion 112 includes a front end portion 112d, a rear end portion 112a, and a watertight resin portion 112c. The front end portion 112d protrudes to the rear from the rear end of the outward protruding portion 113 and contains no silane coupling agent. The rear end portion 112a is arranged at the rear end of the housing 10 and contains no silane coupling agent. The watertight resin portion 112c is arranged between the front end portion 112d and the rear end portion 112a and contains the silane coupling agent.

The watertight resin portion 112c is in close contact with the contacts 20 along the outer peripheries of the contacts 20. The resin constituting the watertight resin portion 112c is of different type from that constituting the plate-like portion 12, the front protruding portion 111, the rear end portion 112a, the front end portion 112d, and the outward protruding portion 113. The resin has a property that its melting temperature is lower than that of the resin constituting the plate-like portion 12, the front protruding portion 111, the rear end portion 112a, the front end portion 112d, and the outward protruding portion 113.

Figure 3:
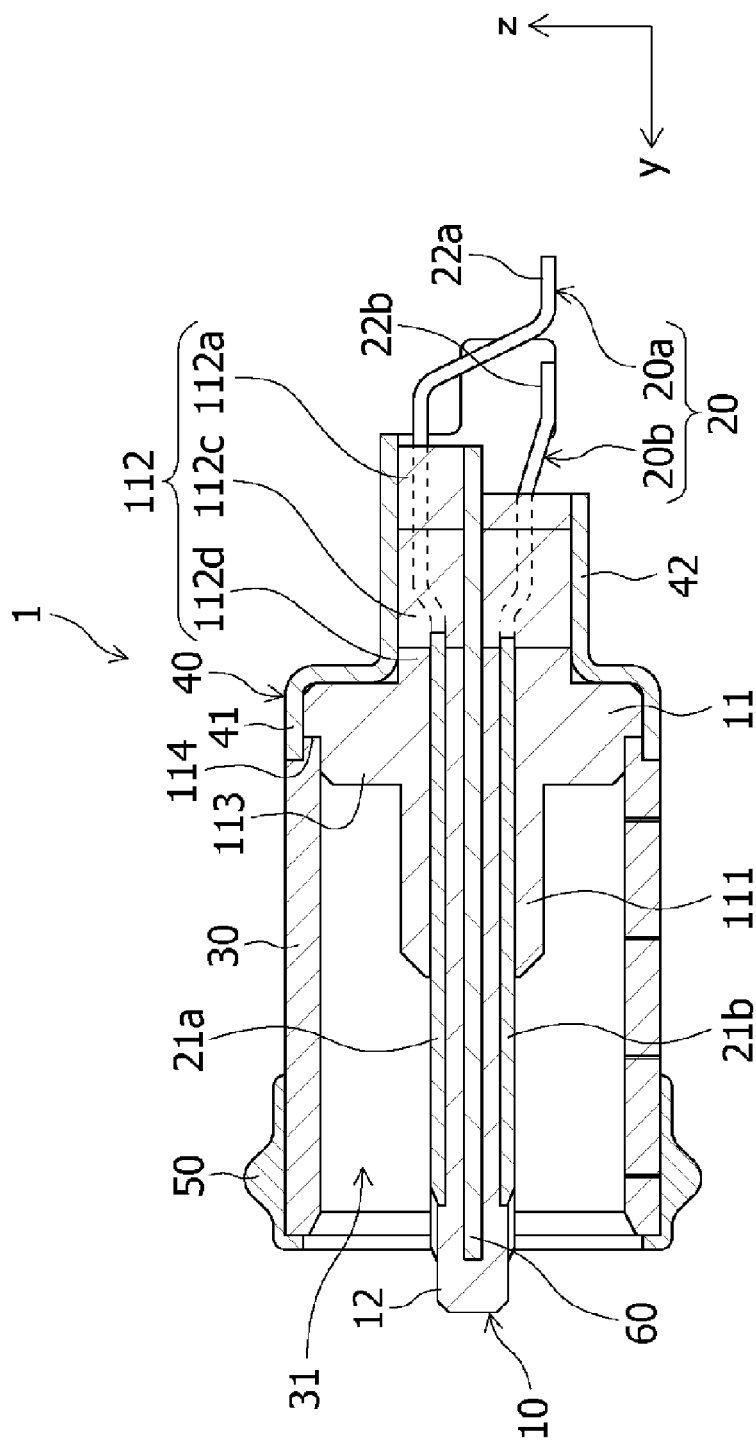
FIG. 3 is a cross-sectional view taken along line A-A of FIG. 2.

For convenience of description, FIG. 3 clearly shows the boundaries between the front end portion 112d, the rear end portion 112a, and the watertight resin portion 112c. In fact, the boundaries are vague since the junction between the front end portion 112d and the watertight resin portion 112c is melted and bonded in a manufacturing step to be described later, and the junction between the rear end portion 112a and the watertight resin portion 112c is melted and bonded in the manufacturing step to be described later.

The plate-like portion 12 has a plate-like shape and protrudes in front of the main body portion 11. The front end side of the plate-like portion 12 protrudes in front of the front shell member 30.

The contacts 20 are formed of a conductive material and held by the housing 10. The contacts 20 include first contacts 20a and second contacts 20b arranged below the first contacts 20a. The first contacts 20a and the second contacts 20b are insulated from each other by the housing 10.

The first contacts 20a each include a connection portion 21a and a terminal portion 22a. The connection portion 21a is exposed on the front side of the housing 10 and exposed in a top surface of the plate-like member 12, and connects to a mating contact of a not-shown mating connector. The terminal portion 22a protrudes behind the housing 10 and is welded to a conductive portion of a not-shown substrate. A part of the first contact 20a between the connection portion 21a and the terminal portion 22a is embedded in the front protruding portion 111, the rear protruding portion 112, and the outward protruding portion 113. The first contact 20a is in close contact with the watertight resin portion 112c along its outer periphery. The part of the first contact 20a in close contact with the watertight resin portion 112c is shaped to bend horizontally and upward.

The second contacts 20b each include a connection portion 21b and a terminal portion 22b. The connection portion 21b is exposed on the front side of the housing 10 and exposed in a bottom surface of the plate-like portion 12, and connects to a mating contact of the not-shown mating connector. The terminal portion 22b protrudes behind the housing 10 and is welded to the not-shown substrate. A part of the second contact 20b between the connection portion 21b and the terminal portion 22b is embedded in the front protruding portion 111, the rear protruding portion 112, and the outward protruding portion 113. The second contact 20b is in close contact with the watertight resin portion 112c along its outer periphery. The part of the second contact 20b in close contact with the watertight resin portion 112c is shaped to bend horizontally and downward. The lower ends of the terminal portions 22a and the lower ends of the terminal portions 22b are vertically at the same height.

The front shell member 30 is formed of a conductive material and has a cylindrical shape extending in a front-to-rear direction. The front shell member 30 includes a fitting portion 31 to which the not-shown mating connector can be fitted from the front. The plate-like portion 12 and the front protruding portion 111 are arranged in the fitting portion 31. The rear end of the front shell member 30 is in contact with the step portion 114 and held on the front side of the outward protruding portion 113.

The rear shell member 40 is made of a conductive material and has a cylindrical shape extending in the front-to-rear direction. The rear shell member 40 includes a large diameter portion 41 and a small diameter portion 42, and has a narrowed shape toward the rear. The large diameter portion 41 is held on the rear side of the outward protruding portion 113. The small diameter portion 42 is continuously formed behind the large diameter portion 41, and has a diameter smaller than that of the large diameter portion 41. The small diameter portion 42 is in close contact with the watertight resin portion 112c along its inner periphery.

The external watertight member 50 is formed of an elastic insulating material in an annular shape, and arranged at the front end of the front shell member 30.

The shielding plate 60 is formed of a conductive material and has a plate-like shape. The shielding plate 60 is embedded in the housing 10. The shielding plate 60 is arranged between the first contacts 20a and the second contacts 20b in a state of being insulated from the first contacts 20a and the second contacts 20b.

<Method for Manufacturing Electrical Connector>

A method for manufacturing the electrical connector 1 according to the first embodiment of the present invention will be described in detail below with reference to FIGS. 1 to 9.

Figure 4:
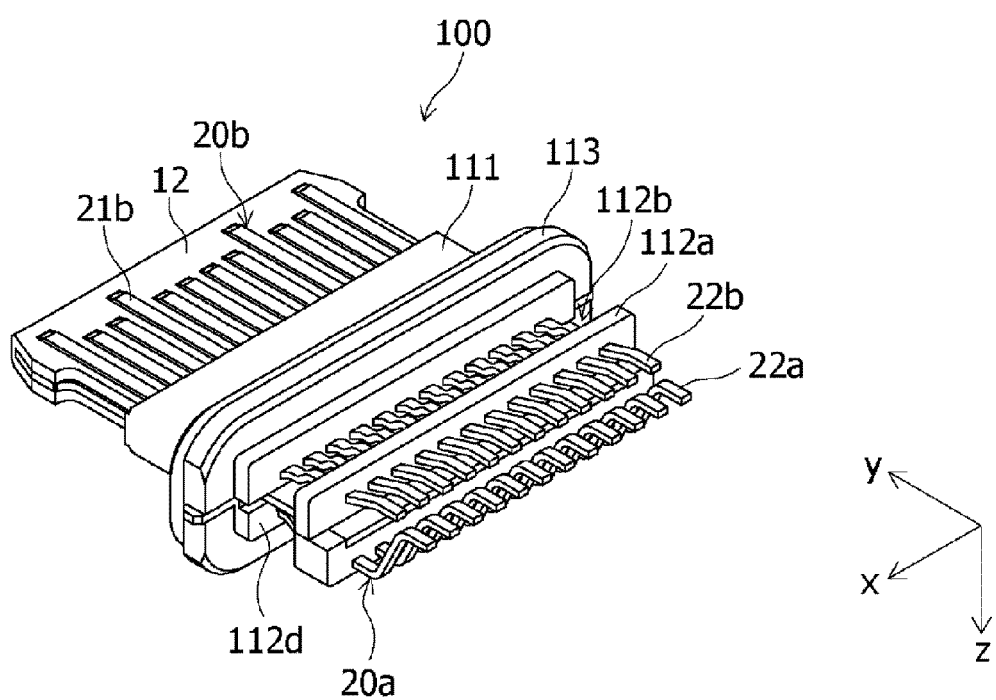
FIG. 4 is a perspective view of a primary molded article constituting the electrical connector according to the first embodiment of the present invention.
Figure 5:
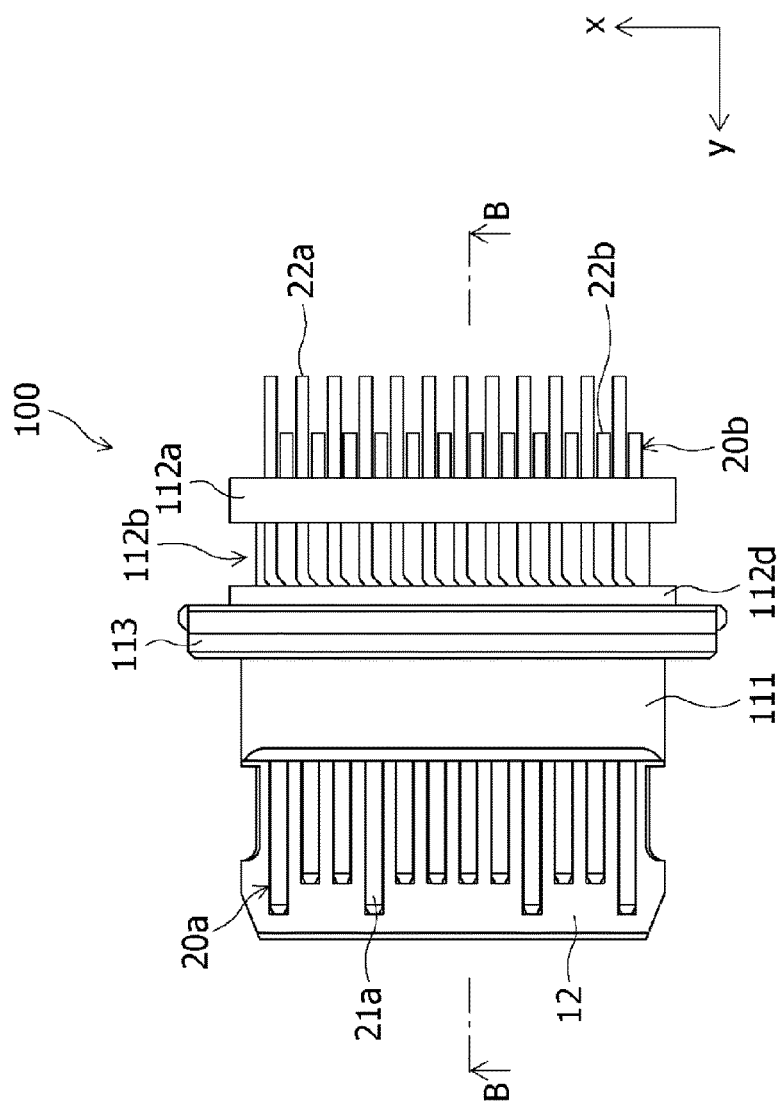
FIG. 5 is a plan view of the primary molded article constituting the electrical connector according to the first embodiment of the present invention.
Figure 6:
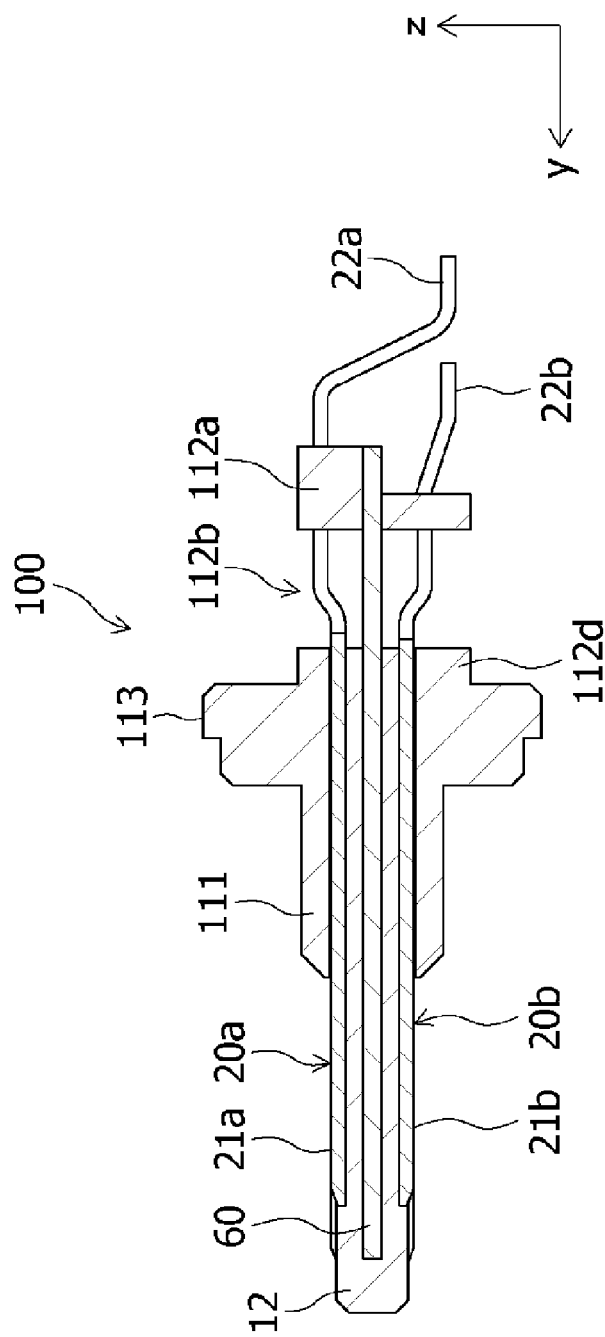
FIG. 6 is a cross-sectional view taken along line B-B of FIG. 5.

The contacts 20 and the shielding plate 60 formed in advance are initially set in a not-shown mold. A resin containing no silane coupling agent is injected into the mold at a predetermined injection molding temperature, followed by curing. By such integral molding, a primary molded article 100 shown in FIGS. 4 to 6 is formed. The primary molded article 100 includes the plate-like portion 12, the contacts 20, the front protruding portion 111, the outward protruding portion 113, the front end portion 112d, the rear end portion 112a, and the shielding plate 60. An example of the injection molding temperature is 300° C.

The primary molded particle 100 has a space 112b between the front end portion 112d and the rear end portion 112a. The front end portion 112d and the rear end portion 112a are opposed to each other. In the space 112b, part of the first contacts 20a and part of the second contacts 20b are exposed to outside.

Figure 7:
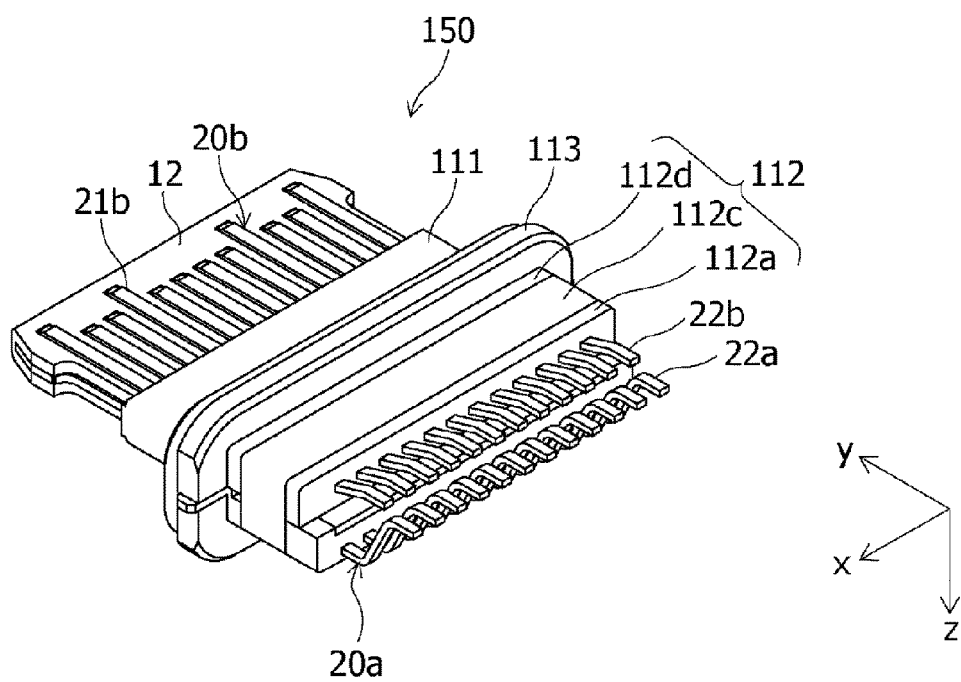
FIG. 7 is a perspective view of a secondary molded article constituting the electrical connector according to the first embodiment of the present invention.
Figure 8:
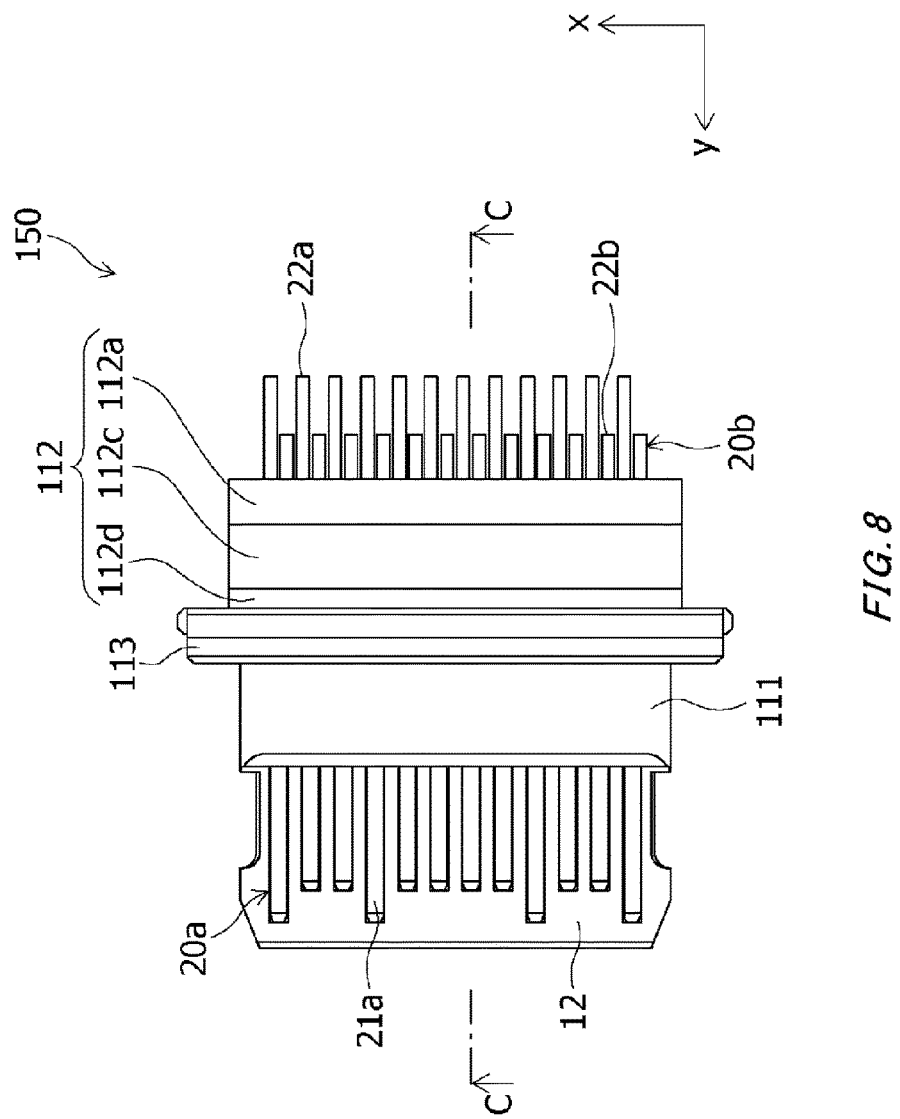
FIG. 8 is a plan view of the secondary molded article constituting the electrical connector according to the first embodiment of the present invention.
Figure 9:
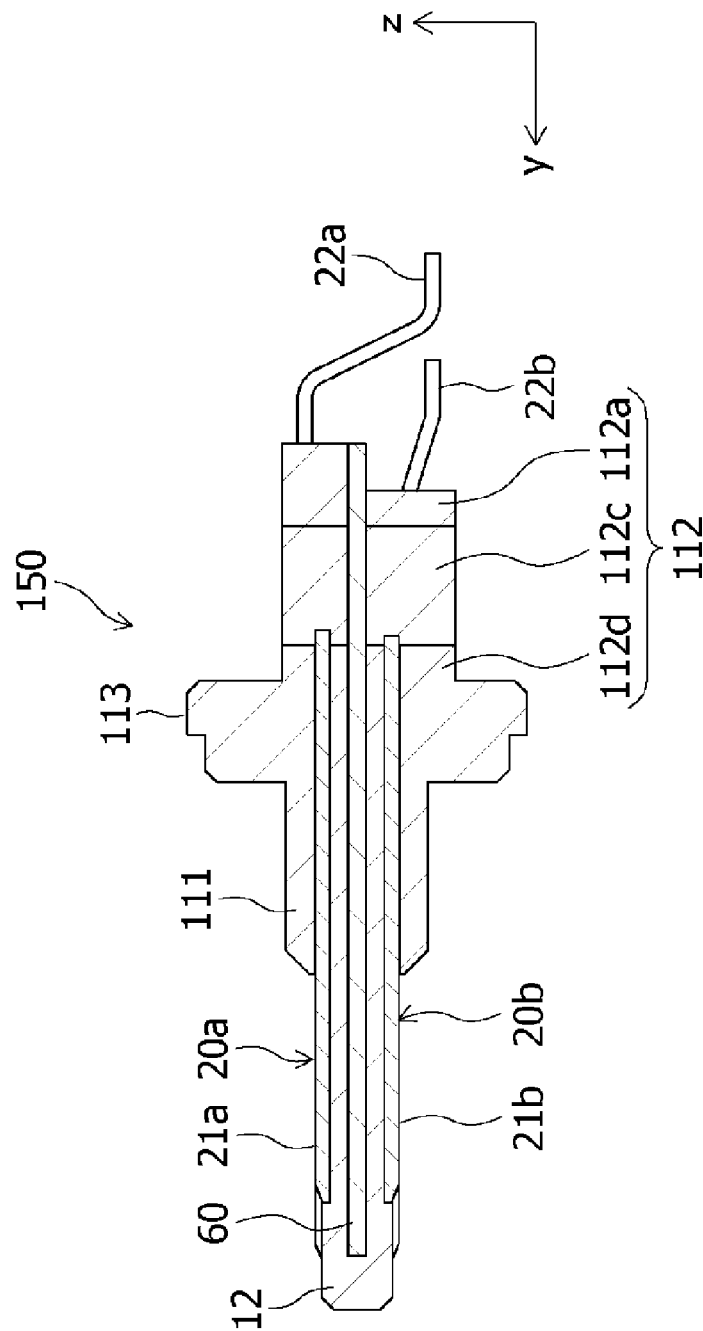
FIG. 9 is a cross-sectional view taken along line C-C of FIG. 8.

Next, the primary molded article 100 is set in a not-shown mold. A resin containing the silane coupling agent is injected into the space 112b at a predetermined temperature, followed by curing. By such integral molding, a secondary molded article 150 shown in FIGS. 7 to 9 is formed. The secondary molded article 150 includes the primary molded article 100 and the watertight resin portion 112c. In other words, the secondary molded article 150 is configured by adding the watertight resin portion 112c to the primary molded article 100.

The resin poured into the space 112b is of different type from that constituting the plate-like portion 12, the front protruding portion 111, the rear end portion 112a, the front end portion 112d, and the outward protruding portion 113 of the primary molded article 100. The resin has a property that its melting point is lower than that of the resin constituting the plate-like portion 12, the front protruding portion 111, the rear end portion 112a, the front end portion 112d, and the outward protruding portion 113 of the primary molded article 100. The temperature in forming the secondary molded article 150 is thus set to be lower than the injection molding temperature in forming the primary molded article 100. An example of the temperature in molding the secondary molded article 150 is 150° C.

Since the temperature in forming the secondary molded article 150 is set to be lower than the injection molding temperature, the resin constituting the plate-like portion 12, the front protruding portion 111, the rear end portion 112a, the front end portion 112d, and the outward protruding portion 113 will not melt when the secondary molded article 150 is formed. In forming the secondary molded article 150, the contacts 20 can thus be securely held by the plate-like portion 12, the front protruding portion 111, the rear end portion 112a, the front end portion 112d, and the outward protruding portion 113. In particular, the contacts 20 can be securely held by the rear end portion 112a. The protruding positions of the terminal portions 22a and 22b from the rear end portion 112a can thus be prevented from shifting when the secondary molded article 150 is formed. This can prevent poor connection of the terminal portions 22a and 22b with the conductive portions of the substrate.

Next, the secondary molded article 150 is covered with the front shell member 30 from the front and covered with the rear shell member 40 from behind.

Next, the front shell member 30 and the rear shell member 40 are attached to the secondary molded article 150 by welding the rear end of the front shell member 30 and the front end of the rear shell member 40.

Next, the external watertight member 50 is attached to the front end of the front shell member 30.

Next, the secondary molded article 150 to which the front shell member 30 and the rear shell member 40 are attached is heated to a temperature higher than that in forming the watertight resin portion 112c, whereby the watertight resin portion 112c is melted again. The temperature to which the secondary molded article 150 having the front shell member 30 and the rear shell member 40 attached thereto is heated may be the same as or different from the injection molding temperature in forming the primary molded article 100.

Here, the part of the watertight resin portion 112c in contact with the outer peripheries of the contacts 20 is melted and bonded to the outer peripheries of the contacts 20 by the bonding action of the silane coupling agent contained in the watertight resin portion 112c. The part of the watertight resin portion 112c in contact with the inner periphery of the rear shell member 40 is melted and bonded to the inner periphery of the rear shell member 40 by the bonding action of the silane coupling agent contained in the watertight resin portion 112c. The watertight resin portion 112c and the outer peripheries of the contacts 20 are thereby put in close contact with each other, and the watertight resin portion 112c and the inner periphery of the rear shell member 40 are put in close contact with each other.

Heating the secondary molded article 150 to which the front shell member 30 and the rear shell member 40 are attached to a temperature higher than that in forming the watertight resin portion 112c can melt at least the watertight resin portion 112c again, whereby the watertight resin portion 112c can be firmly adhered to the rear end portion 112a and the front end portion 112d.

The watertight resin portion 112c thus has adhesiveness to the contacts 20 made of metal and the rear and front end portions 112a and 112d made of a resin material.

Next, the secondary molded article 150 to which the front shell member 30 and the rear shell member 40 are attached is cooled to complete the electrical connector 1.

In the electrical connector 1 manufactured by the foregoing manufacturing method, the watertight resin portion 112c containing the silane coupling agent makes close contact with the outer peripheries of the contacts 20 to seal the gaps between the watertight resin portion 112c and the contacts 20. The interior of an electronic device to which the electrical connector 1 is attached can thus be sealed off from the gaps between the housing 10 and the contacts 20 and made watertight. In the electrical connector 1, the watertight resin portion 112c containing the silane coupling agent makes close contact with the inner periphery of the rear shell member 40 to seal the gap between the watertight resin portion 112c and the rear shell member 40. The interior of the electronic device to which the electrical connector 1 is attached can thus be sealed off from the gap between the housing 10 and the rear shell member 40 and made watertight.

In the foregoing manufacturing method, the watertight resin portion 112c is formed before the front shell member 30 and the rear shell member 40 are provided. However, the front shell member 30 and the rear shell member 40 may be provided before the formation of the watertight resin portion 112c. A resin containing the silane coupling agent may be injected into the space 112b through a gap of the rear shell member 40 and then heated to form the watertight resin portion 112c.

As described above, according to the present embodiment, a portion of the housing 10 in close contact with the contacts 20 along the outer peripheries of the contacts 20 contains the silane coupling agent. The gaps between the housing 10 and the contacts 20 can thus be made watertight. This can eliminate the need for elastic parts and potting agents for sealing to simplify assembly. An increase in manufacturing cost can be suppressed as well.

According to the present embodiment, a portion of the housing 10 in close contact with the rear shell member 40 along the inner periphery of the rear shell member 40 contains the silane coupling agent. The gap between the housing 10 and the rear shell member 40 can thus be made watertight. This can simplify assembly and suppress an increase in manufacturing cost.

While the present embodiment includes the external watertight member 50, the external watertight member 50 does not need to be provided.

In the present embodiment, two types of contacts, namely, the first contacts 20a and the second contacts 20b are arranged on the housing 10. However, one type of contacts may be arranged on the housing.

While the present embodiment includes the shielding plate 60, the shielding plate 60 does not need to be provided.

In the present embodiment, the housing 10 may have any shape as long as the silane coupling agent-containing part of the housing makes close contact along the outer peripheries of the contacts 20 and makes close contact along the inner periphery of the rear shell member 40.

In the present embodiment, the front shell member 30 and the rear shell member 40 are formed of a conductive material. However, either one or both of the front and rear shell members 30 and 40 may be formed of an insulating material.

In the present embodiment, the shell member includes two members, namely, the front shell member 30 and the rear shell member 40. However, the shell member may be configured as a single member.

Second Embodiment

<Configuration of Electrical Connector>

Figure 10:
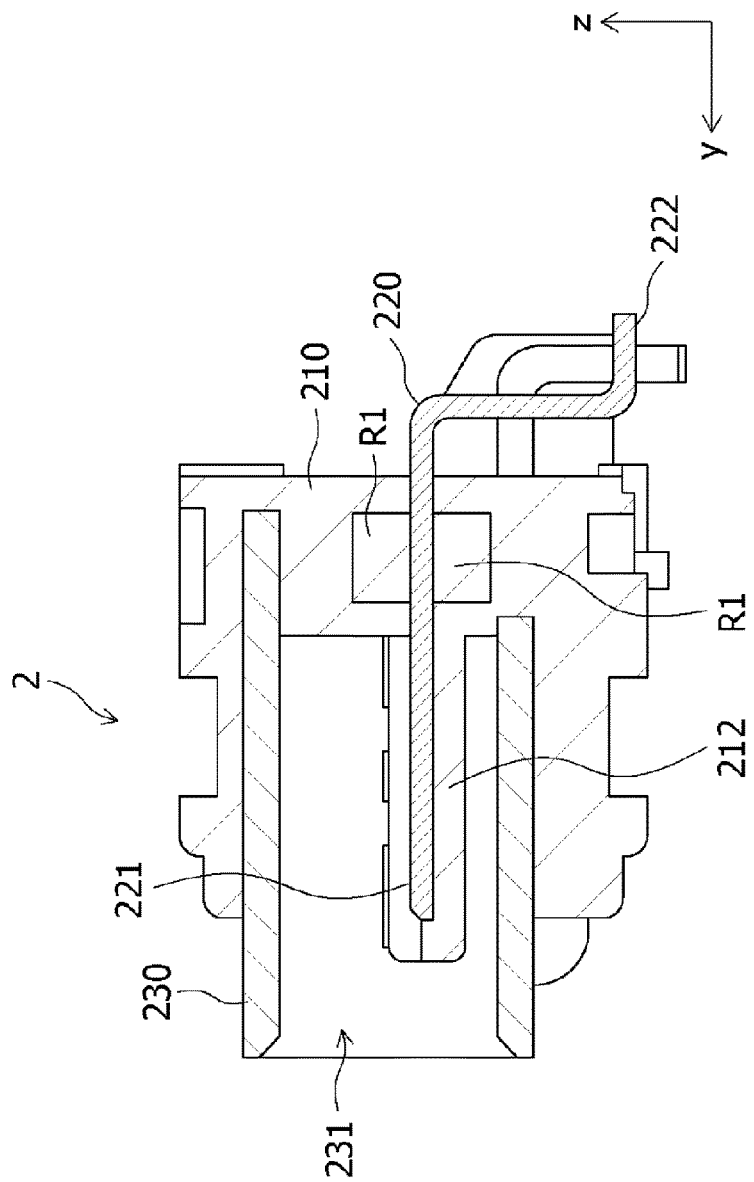
FIG. 10 is a cross-sectional view of an electrical connector according to a second embodiment of the present invention.

A configuration of an electrical connector 2 according to a second embodiment of the present invention will be described in detail below with reference to FIG. 10.

The electrical connector 2 according to the present embodiment includes a housing 210, contacts 220, and a shell member 230.

The housing 210 is formed of an insulating material and holds the contacts 220. The housing 210 contains a silane coupling agent in its watertight resin portion R1 which is a portion to make close contact with the contacts 220 along the outer peripheries of the contacts 220. The housing 210 includes a plate-like portion 212 of plate-like shape protruding to the front.

The contacts 220 are formed of a conductive material and held by the housing 210. The contacts 220 each include a connection portion 221 and a terminal portion 222. The connection portion 221 is exposed to the front and exposed in a top surface of the plate-like portion 212. The connection portion 221 connects to a mating contact of a not-shown mating connector. The terminal portion 222 protrudes behind the housing 210 and is welded to a conductive portion of a not-shown substrate. A part of the contact 220 between the connection portion 221 and the terminal portion 222 is embedded in the housing 210 and makes close contact with the portion R1.

The shell member 230 is formed of a conductive material and has a cylindrical shape extending in a front-to-rear direction. The shell member 230 includes a fitting part 231 in which the plate-like portion 212 is arranged and to which the not-shown mating connector can be fitted from the front. The rear end of the shell member 230 is held by the housing 210.

<Method for Manufacturing Electrical Connector>

A method for manufacturing the electrical connector 2 according to the second embodiment of the present invention will be described in detail below.

Initially, the contacts 220 and the watertight resin portion R1 containing the silane coupling agent are integrally molded at a predetermined temperature to form a primary molded article. An example of the predetermined temperature is 150° C.

Next, the primary molded article and the shell member 230 are set in a not-shown mold. A resin containing no silane coupling agent is injected into the mold at a predetermined injection molding temperature, followed by curing. By such integral molding, the electrical connector 2 is formed. An example of the injection molding temperature is 300° C.

The injection molding temperature is higher than the predetermined temperature in forming the foregoing primary molded article. The part of the watertight resin portion R1 in contact with the outer peripheries of the contacts 220 is thus melted again and bonded to the outer peripheries of the contacts 220 by the bonding action of the silane coupling agent contained in the watertight resin portion R1. The watertight resin portion R1 and the outer peripheries of the contacts 220 are thereby put in close contact with each other. Melting the watertight resin portion R1 again firmly adheres the watertight resin portion R1 to the portions of the housing 210 other than the watertight resin portion R1.

The watertight resin portion R1 thus has adhesiveness to the metal contacts 220 and the portions of the resin housing 210 other than the watertight resin portion R1.

In the electrical connector 2 manufactured by the foregoing manufacturing method, the watertight resin portion R1 containing the silane coupling agent makes close contact with the outer peripheries of the contacts 220 to seal the gaps between the watertight resin portions R1 and the contacts 220. The interior of an electronic device to which the electrical connector 2 is attached can thus be sealed off from the gaps between the housing 210 and the contacts 220 and made watertight.

As described above, according to the present embodiment, the portion of the housing 210 in close contact with the contacts 220 along the outer peripheries of the contacts 220 contains the silane coupling agent. The gaps between the housing 210 and the contacts 220 can thus be made watertight. This can eliminate the need for elastic parts and potting agents for sealing to simplify assembly. An increase in manufacturing cost can be suppressed as well.

According to the present embodiment, the watertight resin portion R1 can provide the watertight effect in the step of integrally molding the primary molded article and the shell member 230. Such a configuration can simplify the assembly steps to facilitate manufacturing, with a reduction in manufacturing cost.

The present invention is not limited to the foregoing embodiments in terms of the types, arrangement, numbers, or the like of the members. It will be understood that appropriate modifications may be made without departing from the gist of the invention. For example, the components may be replaced with ones having similar operations and effects as appropriate.

The embodiment of the present invention is suitable for an electrical connector having a watertight function and a method for manufacturing the electrical connector.

REFERENCE SIGNS LIST 1 electrical connector
2 electrical connector
10 housing
11 main body portion
12 plate-like portion
20 contact
20a first contact
20b second contact
21a connection portion
21b connection portion
22a terminal portion
22b terminal portion
30 front shell member
31 fitting portion
40 rear shell member
41 large diameter portion
42 small diameter portion
50 external watertight member
60 shielding plate
100 primary molded article
111 front protruding portion
112 rear protruding portion
112a rear end portion
112b space
112c watertight resin portion
112d front end portion
113 outward protruding portion
114 step portion
150 secondary molded article
210 housing
212 plate-like portion
220 contact
221 connection portion
222 terminal portion
230 shell member
231 fitting part
R1 watertight resin portion

The invention claimed is:

1. An electrical connector comprising:
an insulating housing; and
a conductive contact held by the housing, the contact including a connection portion that is exposed on a front side of the housing and connects to a mating contact of a mating connector, and a terminal portion that protrudes behind the housing,
two adjacent portions of the housing being in close contact with the contact along an outer periphery of the contact, one of the two adjacent portions of the housing containing a silane coupling agent, and the other one of the two adjacent portions not containing a silane coupling agent.

2. The electrical connector according to claim 1, further comprising a cylindrical shell member configured to cover a periphery of the housing, wherein
the one of the two adjacent portions of the housing is in close contact with the shell member along an inner periphery of the shell member.

3. The electrical connector according to claim 1, wherein
a third portion of the housing is adjacent to the first one of the two adjacent portions of the housing, the third portion of the housing not containing a silane coupling agent, the third portion of the housing being in a rear end portion thereof where the contact protrudes rearward.

4. A method for manufacturing an electrical connector, the electrical connector including an insulating housing and a conductive contact held by the housing, the contact including a connection portion that is exposed on a front side of the housing and connects to a mating contact of a mating connector, and a terminal portion that protrudes behind the housing, the method comprising:
integrally molding the housing and the contact, the housing being formed of a first housing containing a silane coupling agent and a second housing containing no silane coupling agent, and simultaneously forming the first housing holding the contact at a predetermined temperature; and
melting the first housing, after formed, again at a temperature higher than the predetermined temperature so that the first housing makes close contact with the contact along an outer periphery of the contact.

5. An electrical connector comprising:
an insulating housing including a front protruding portion that protrudes to front, a rear protruding portion that protrudes to rear, and an outward protruding portion that lies between the front protruding portion and the rear protruding portion and protrudes outward compared to the front protruding portion and the rear protruding portion;
a conductive contact held by the housing, the contact including a connection portion that is exposed on a front side of the housing and connects to a mating contact of a mating connector, and a terminal portion that protrudes behind the housing; and
a cylindrical shell member configured to cover a periphery of the housing, wherein
the shell member is configured with a front shell member and a rear shell member, the front shell member including a fitting portion to which the mating connector is fitted from the front and being held on the front side of the outward protruding portion, and the rear shell member being held on the rear side of the outward protruding portion, and the rear shell member includes a large diameter portion that is held on the rear side of the outward protruding portion and a small diameter portion that is continuously formed behind the large diameter portion and has a diameter smaller than a diameter of the large diameter portion.

6. A method for manufacturing an electrical connector, the electrical connector including (i) an insulating housing including a front protruding portion that protrudes to front, a rear protruding portion that protrudes to rear, and an outward protruding portion that lies between the front protruding portion and the rear protruding portion and protrudes outward compared to the front protruding portion and the rear protruding portion; (ii) a conductive contact held by the housing, the contact including a connection portion that is exposed on a front side of the housing and connects to a mating contact of a mating connector, and a terminal portion that protrudes behind the housing; and (iii) a cylindrical shell member configured to cover a periphery of the housing, wherein the shell member is configured with a front shell member and a rear shell member, the front shell member including a fitting portion to which the mating connector is fitted from the front and being held on the front side of the outward protruding portion, and the rear shell member being held on the rear side of the outward protruding portion, and the rear shell member includes a large diameter portion that is held on the rear side of the outward protruding portion and a small diameter portion that is continuously formed behind the large diameter portion and has a diameter smaller than a diameter of the large diameter portion, the method comprising:

attaching the front shell member and the rear shell member to the housing by covering the housing with the front shell member from the front and covering the housing with the rear shell member from behind.

* * * * *